United States Patent
Arya et al.

(10) Patent No.: US 9,433,665 B2
(45) Date of Patent: Sep. 6, 2016

(54) VACCINES FOR PROTECTION FROM AND TREATMENT OF ALZHEIMER'S DISEASE

(71) Applicant: Cyvax, Inc., Atlanta, GA (US)

(72) Inventors: Bira Arya, Ellicott City, MD (US); Richard Markham, Columbia, MD (US)

(73) Assignee: Cyvax, Inc., Atlanta, GA (US)

( * ) Notice: Subject to any disclaimer, the term of this patent is extended or adjusted under 35 U.S.C. 154(b) by 0 days.

(21) Appl. No.: 14/152,782

(22) Filed: Jan. 10, 2014

(65) Prior Publication Data

US 2014/0199338 A1    Jul. 17, 2014

Related U.S. Application Data

(60) Provisional application No. 61/751,769, filed on Jan. 11, 2013, provisional application No. 61/752,322, filed on Jan. 14, 2013.

(51) Int. Cl.
| | |
|---|---|
| *A61K 39/00* | (2006.01) |
| *A61K 48/00* | (2006.01) |
| *C12N 5/10* | (2006.01) |
| *A01K 67/00* | (2006.01) |
| *A01K 67/027* | (2006.01) |

(52) U.S. Cl.
CPC ... *A61K 39/0007* (2013.01); *A61K 2039/5256* (2013.01); *A61K 2039/53* (2013.01); *A61K 2039/545* (2013.01); *A61K 2039/55522* (2013.01); *A61K 2039/6075* (2013.01); *C12N 2730/10143* (2013.01)

(58) Field of Classification Search
CPC .............. A61K 2039/5256; A61K 2039/53; A61K 2039/545; A61K 2039/55522
See application file for complete search history.

(56) References Cited

U.S. PATENT DOCUMENTS 7,811,576 B2 * 10/2010 Milich et al. .............. 424/189.1

FOREIGN PATENT DOCUMENTS

| WO | WO2005067966 | * | 7/2005 |
| WO | WO2012021558 | * | 2/2012 |

OTHER PUBLICATIONS

Gao et al., "nonviral gene delivery: what we know and what is next", 2007, The AAPS Journal, 9(1):E92-E104.*
Zhang et al., "In vivo gene delivery by nonviral vectors: overcoming hurdles", 2012, molecular therapy, 20(7):1298-1304.*
Niidome et al., "Gene therapy progress and prospects: nonviral vectors", 2002, Gene Therapy, 9:1647-1652.*
Tejedor et al., "Current animal models of Alzheimer's disease: challenges in translational research", 2014, Frontiers in Neurology, 5:1-2.*
Alavez, S., et al., "Amyloid-Binding Compounds Maintain Protein Homeostasis During Aging and Extend Lifespan," Nature 472:226-229, 2011.
Bacskai, B.J., et al., "Non-Fc-Mediated Mechanisms are Involved in Clearance of Amyloid-βin Vivo by Immunotherapy," J. Neurosci. 22:7873-7878, 2002.
Biragyn, A., et al., "DNA Vaccines Encoding Human Immunodeficiency Virus-1 Glycoprotein 120 Fusions with Proinflammatory Chemoattractants Induce Systemic and Mucosal Immune Responses," Blood 100:1153-1159, 2002.
Biragyn, A., et al., "Mediators of Innate Immunity that Target Immature, but not Mature, Dendritic Cells Induce Antitumor Immunity when Genetically Fused with Nonimmunogenic Tumor Antigens," J. Immunol. 167:6644-6653, 2001.
Boche, D., et al., "Consequence of Aβ Immunization on the Vasculature of Human Alzheimer's Disease Brain," Brain 131:3299-3310, 2008.
Hartikka, J., et al., "Vaxfectin Enhances the Humoral Immune Response to Plasmid DNA-Encoded Antigens," Vaccine 19:1911-1923, 2001.
Holmes, C., et al., "Long-term effects of $A\beta_{42}$ immunisation in Alzheimer's disease: follow-up of a randomised, placebo-controlled phase I trial," Lancet 372:216-223, 2008.
Milich, D.R., et al., "Preferential Recognition of Hepatitis B Nucleocapsid Antigens by $Th_1$ or $Th_2$ Cells is Epitope and Major Histocompatibility Complex Dependent," J. Virol. 69:2776-2785, 1995.
Olkhanud P., et al., "DNA immunization with HBsAg-based particles expressing a B cell epitope of amyloid β-peptide attenuates disease progression and prolongs survival in a mouse model of Alzheimer's disease," Vaccine. 30(9): 1650-1658, 2012.
Ruffini, P.A., et al., "Idiotypic Vaccination for B-Cell Malignancies as a Model for Therapeutic Cancer Vaccines: from Prototype Protein to Second Generation Vaccines," Haematologica 87:989-1001, 2002.
Wilcock, D.M., et al., "Passive Amyloid Immunotherapy Clears Amyloid and Transiently Activates Microglia in a Transgenic Mouse Model of Amyloid Deposition," J. Neurosci. 24:6144-6151, 2004.
Yang, D., et al., "β-Defensins: Linking Innate and Adaptive Immunity Through Dendritic and T Cell CCR6," Science 286:525-528, 1999.

* cited by examiner

*Primary Examiner* — Janet L Andres
*Assistant Examiner* — Barry A Chestnut
(74) *Attorney, Agent, or Firm* — Latimer IPLaw, LLC

(57) ABSTRACT

Disclosed herein are DNA-based vaccines against amyloid β peptide for use in treating and alleviating Alzheimer's Disease and related conditions. A DNA construct comprising DNA encoding one or more amyloid β peptides, such as amino acids 1-11 of Aβ, and DNA encoding a hepatitis B antigens, is administered with an adjuvant or by electroporation. The vaccine can also be formulated using a fusion protein expressed by the disclosed DNA, in combination with an adjuvant.

20 Claims, 8 Drawing Sheets

VACCINES FOR PROTECTION FROM AND TREATMENT OF ALZHEIMER'S DISEASE

CROSS REFERENCE TO RELATED APPLICATIONS

This application claims the benefit under 35 U.S.C. §119(e) to U.S. Provisional Patent Applications 61/751,769 filed Jan. 11, 2013 and 61/752,322 filed Jan. 14, 2013, the entire disclosures of which are incorporated by reference herein in their entirety.

FIELD OF THE DISCLOSURE

DNA-based vaccines against pathology-related proteins, including proteins involved in Alzheimer's Disease, are disclosed herein.

BACKGROUND OF THE DISCLOSURE

Alzheimer's disease (or Alzheimer Disease, AD) is a common disorder of the elderly that currently affects over 5 million Americans. It is an incurable and progressive neurodegenerative senile disorder. Although the primary cause(s) of AD is unknown, the disease process involves the progressive extracellular accumulation of aggregated forms of amyloid β peptide (Aβ or Abeta) into plaques in the brain, and associated intracellular deposits of hyperphosphorylated tau protein and brain atrophy. AD patients exhibit progressive cognitive and emotional/behavioral impairments as a result of synaptic dysfunction and neuronal degeneration in multiple interconnected brain regions including the hippocampus, frontal cortex and amygdala.

Studies of experimental cell culture and animal models of AD suggest that the neurotoxic activity of Aβ occurs when Aβ is in an oligomeric form, and involves membrane-associated oxidative stress that impairs synaptic plasticity and memory and causes neuritic and tau hyperphosphorylation. The accumulation of Aβ can also trigger the induction of harmful inflammatory responses that involve the activation of microglia and astrocytes and cause infiltration of Aβ-specific T cells into the brain (Aβ contains a number of human and mouse T cell epitopes in its 15-42 amino acid portion), and may eventually lead to patho-neurophysiological impairments and death.

There is a great need for AD vaccines, especially for those that are effective in middle- to old-aged individuals. Preclinical studies have demonstrated that Aβ deposits can be reduced by passive administration of Aβ-specific antibody or by active immunization with Aβ(1-42) peptide. For example, in a clinical trial of active Aβ immunization (vaccine AN1792) in AD patients, generation of anti-Aβ antibody was associated with a slower rate of decline of cognitive functions in those patients. However, only about 70% of the test subjects were antibody responders, despite repeated immunizations. Although vaccines that reduce Aβ plaques can control AD, the rationale for their use at the onset of the disease remains debatable. For example, older humans and mice usually respond poorly to vaccines generally, due to an age-related decline in immunity and associated immunological impairments. Moreover, chronic exposure to Aβ may also induce AD vaccine or antibody hyporesponsiveness. This may explain the inability of 3xTgAD mice to generate antibody when immunized with Aβ(1-42) peptide, and the relatively poor response demonstrated in AD patients to AN1792. Safety concerns with prior vaccines may preclude the feasibility of AD immunizations in apparently healthy people prior to diagnosis/onset of AD. For example, an AN1792 vaccine trial was prematurely halted because a subset of patients developed T-cell mediated meningoencephalitis, attributed to the induction and infiltration of Aβ-specific T cells.

Accordingly, there is a continued need in the art for compositions and methods to safely prevent and/or slow the progress of AD and to improve the quality of life of sufferers.

SUMMARY OF THE DISCLOSURE

The present disclosure helps to meet the need for a vaccine to alleviate Alzheimer's Disease by providing a DNA vaccine that can comprise a DNA plasmid containing and expressing in vivo a polynucleotide, wherein the polynucleotide comprises (i) polynucleotide sequence encoding an antigenic polypeptide; (ii) a polynucleotide sequence encoding a T-helper epitope of hepatitis B virus capsid antigen; and, (iii) S gene of hepatitis B virus, wherein the antigenic peptide comprises amyloid-β protein or a fragment thereof.

Also provided is a DNA vaccine comprising a DNA plasmid containing and expressing in vivo a polynucleotide encoding (i) amino acids 1-11 of amyloid-β protein, (ii) a T-helper epitope of hepatitis B virus capsid antigen, and (iii) hepatitis B virus surface antigen.

Further provided is a DNA vaccine comprising a DNA plasmid containing and expressing in vivo a polynucleotide, wherein the polynucleotide comprises (i) a polynucleotide sequence encoding an antigenic polypeptide; (ii) a polynucleotide sequence encoding a T-helper epitope of hepatitis B capsid antigen; and, (iii), a polynucleotide of the S gene of hepatitis B virus, wherein the antigenic peptide comprises amyloid-β protein or a fragment thereof, and wherein the vaccine comprises at least one adjuvant.

Provided in some embodiments herein is a DNA vaccine comprising a DNA plasmid containing and expressing in vivo a polynucleotide, wherein the polynucleotide comprises (i) a polynucleotide sequence encoding an antigenic polypeptide of SEQ ID NO:1; (ii) a polynucleotide sequence encoding T-helper epitope of hepatitis B virus capsid antigen of SEQ ID NO:2; and, (iii) S gene of hepatitis B virus.

The DNA vaccine as disclosed herein can comprise DNA encoding (i) Aβ antigen, (ii) T-helper epitope of hepatitis B capsid antigen, (iii) hepatitis B surface antigen, and (iv) a chemokine that targets immature dendritic cells, wherein the chemokine can bind to the CCR2, or CCR5, and/or CCR6 receptor on the dendritic cells.

In the DNA vaccines provided herein, the antigenic polypeptide can have the amino acid sequence of SEQ ID NO:1. In some embodiments of the DNA vaccines provided herein, the T-helper epitope of hepatitis B virus capsid antigen can have the amino acid sequence of SEQ ID NO:2. In some embodiments of the DNA vaccines provided herein, the DNA vaccine comprises a polynucleotide encoding the amino acid sequence of SEQ ID NO:3. In some embodiments of the DNA vaccines provided herein, the DNA vaccine comprises the polynucleotide sequence represented by SEQ ID NO:4.

The provided DNA vaccine can comprise DNA encoding an Aβ antigen and DNA encoding macrophage inhibitory protein 3α (MIP-3α).

Any of the disclosed DNA vaccines can be used in combination with an adjuvant that is a cationic liposome; the cationic liposome used in combination with the DNA vaccines can be VAXFECTIN® (Vical, Inc., San Diego, Calif.).

In certain embodiments, the polynucleotide further comprises a ligand, wherein the ligand is a molecule which binds immature dendritic cells. In another embodiment, the chemokine binds to the CCR2, CCR5, and/or CCR6 receptor on the dendritic cells. In another embodiment, the ligand is a human β-defensin.

In another embodiment, the DNA vaccine further comprises an adjuvant, such as an adjuvant comprising a cationic lipid and a neutral phospholipid in an aqueous vehicle.

Also provided are methods of sustaining or preventing the decline of cognitive function, sustaining or preventing the decline of emotional and behavioral components of the disease and/or increasing survival in a human afflicted with Alzheimer's Disease and methods of reducing Aβ plaques in a human afflicted with Alzheimer's Disease, the methods comprising administering to the human a DNA vaccine as disclosed.

Also provided is a method of extending life span in a mammal, said method comprising administering to said mammal a DNA vaccine of the disclosure, wherein the mammal can be a human.

Also provided is a method of treating a human for Alzheimer's Disease, wherein the treating is (a) reducing the severity of Alzheimer's Disease in a human; (b) increasing survival; (c) reducing Aβ plaques in a human afflicted with Alzheimer's Disease; (d) reducing the severity of Alzheimer's Disease in a human at risk of said disease; and/or (e) extending life span of said human, said method comprising administering to said human a DNA vaccine disclosed herein In another embodiment, the vaccine is administered more than once. In another embodiments, an antibody titer to the antigen in the blood is measured after vaccination to determine the need for additional vaccine administration. In yet another embodiment, the vaccine is administered prior to onset of symptoms.

BRIEF DESCRIPTION OF THE DRAWINGS

FIG. 1A is a graph showing that DNA immunizations with HBsAg (S) or HBsAg fused with MC148 (MC148-S) only induce high levels of anti-HBsAg antibody in young, but not old, C57BL/6 mice. FIG. 1B is a series of three Immunogold-electron microscopy images of Aβ-CoreS showing that Aβ is exposed on the surface of 24-36 nm particles. Aβ-CoreS expressed in yeast was partially purified by silica gel absorption. The samples were untreated (control) or stained with control antibody (IgG) or Aβ-specific antibody 6E10. Bar indicates 50 nm. FIG. 1C is a graph showing that immunizations with Aβ-CoreS generated comparably high levels of antibody to HBsAg in both young and old C57BL/6 mice in a side-by-side experiment. FIG. 1D is a graph showing that Aβ-CoreS vaccine also generated comparably levels of anti-Aβ antibody in young and old C57BL/6 mice in a side-by-side experiment. The Y-axis shows relative concentration ($OD_{450}$) of antibody in sera of mice DNA immunized three times, as detected by ELISA. X-axis shows serum titration.

FIG. 2A is a graph showing that Aβ-CoreS generated high levels of anti-Aβ antibody in both wild-type (WT) and 3xTgAD mice, when immunizations were started at 12 month-old age. In contrast, the ability of Aβ(1-42) peptide to generate anti-Aβ antibody in WT was lost in 12 month-old 3xTgAD in a side-by-side experiment. FIG. 2B and FIG. 2C show that the majority of antibody generated in Aβ-CoreS immune young (FIG. 2B) and old (FIG. 2C) 3xTgAD mice was IgG2b (data of a side-by-side experiment). Control immunizations with S antigen (right panel) did not generate Aβ-specific antibody (FIG. 2B, FIG. 2C). The Y-axis shows relative concentration ($OD_{450}$) of antibody serially diluted sera (X-axis) of at least four mice per group, DNA-immunized three times, as detected by ELISA.

FIG. 3 shows that immunizations with Aβ-CoreS induced Aβ-specific T cell responses in young (FIG. 3A, FIG. 3B) and old (FIG. 3C, FIG. 3D) C57BL/6 mice. In contrast, T cells from mice immunized with a full-length Aβ(1-42) peptide readily proliferated upon incubation with Aβ peptide (Aβ(1-42) peptide in FIGS. 3A and 3C, and grey bars in FIGS. 3B and 3D). Carboxyfluorescein succinimidyl ester (CFSE)-labeled splenocytes were stimulated with 2 μg Aβ(1-42) peptide or control g100 peptide (Mock) for 7 days. Numbers in the dot histograms of CFSE dilution assay (FIGS. 3A and 3C) show a representative proportion of proliferated T cells of a summary graph (FIGS. 3B and 3D). Y-axis shows T cell proliferation, presented as a fold increase compared with untreated controls (FIGS. 3B and 3D) of CFSE diluted cells±SEM of triplicate experiments. No specific T cell responses were detected in control mice injected with PBS.

FIG. 4 shows that Aβ-CoreS immunization reduced Aβ plaques in hippocampus of 3xTgAD mice, as shown by immunohistochemistry staining (FIG. 4A, FIG. 4B) or western blot hybridization (FIG. 4C, FIG. 4D) with 6E10 antibody. FIG. 4A and FIG. 4C show a representative picture of average levels of Aβ plaques±SEM in five (FIG. 4B) and two individual mouse samples each (FIG. 4C), respectively. Data are from 15 month-old 3xTgAD mice immunized intradermally (i.d.) three times with 25 μg DNA encoding Aβ-CoreS starting at 12 months of age. Control mice were immunized with 25 μg DNA encoding HBsAg (Mock), or 10 μg Aβ(1-42) peptide subcutaneously (s.c.) in incomplete Freund's adjuvant (IFA) (FIG. 4C) or in alum (FIG. 4D, Aβ peptide), or adjuvant alone, IFA (FIG. 4C) and alum (FIG. 4D).

FIG. 5 shows that the reduction of Aβ plaques is associated with enhanced freezing behavior in the hippocampus-dependent contextual fear conditioning task (FIG. 5A); and decreased anxiety of 3xTgAD mice (as evident by reduced time spent in the open arm of the elevated plus maze; seconds, FIG. 5B). The relatively short life span of 3xTgAD mice was significantly enhanced by immunizing with Aβ-CoreS (FIG. 5C). The mice were mock treated or immunized with Aβ-CoreS when they were 1 and 1.5 years old, respectively, and observed until they reached 28 months old (FIG. 5C). Survival benefit of the Aβ-CoreS vaccine was lost when immunizations started at 22 months of age in surviving 3xTgAD mice (FIG. 5D). Shown, average±SEM of 8 mice (FIG. 5A-C, $P<0.05$) and 4 mice (FIG. 5D) per group experiments comparing Aβ-CoreS and mock immunizations.

FIG. 6 is a bar graph showing that the disclosed vaccine Aβ-CoreS did not elicit Aβ-specific T cell responses (Proliferated T cells (%)) in triple transgenic mice with AD (3xTgAD), compared to immunization with a full length Aβ (1-42) peptide, which readily induced T cell responses.

DETAILED DESCRIPTION

Figure 1:
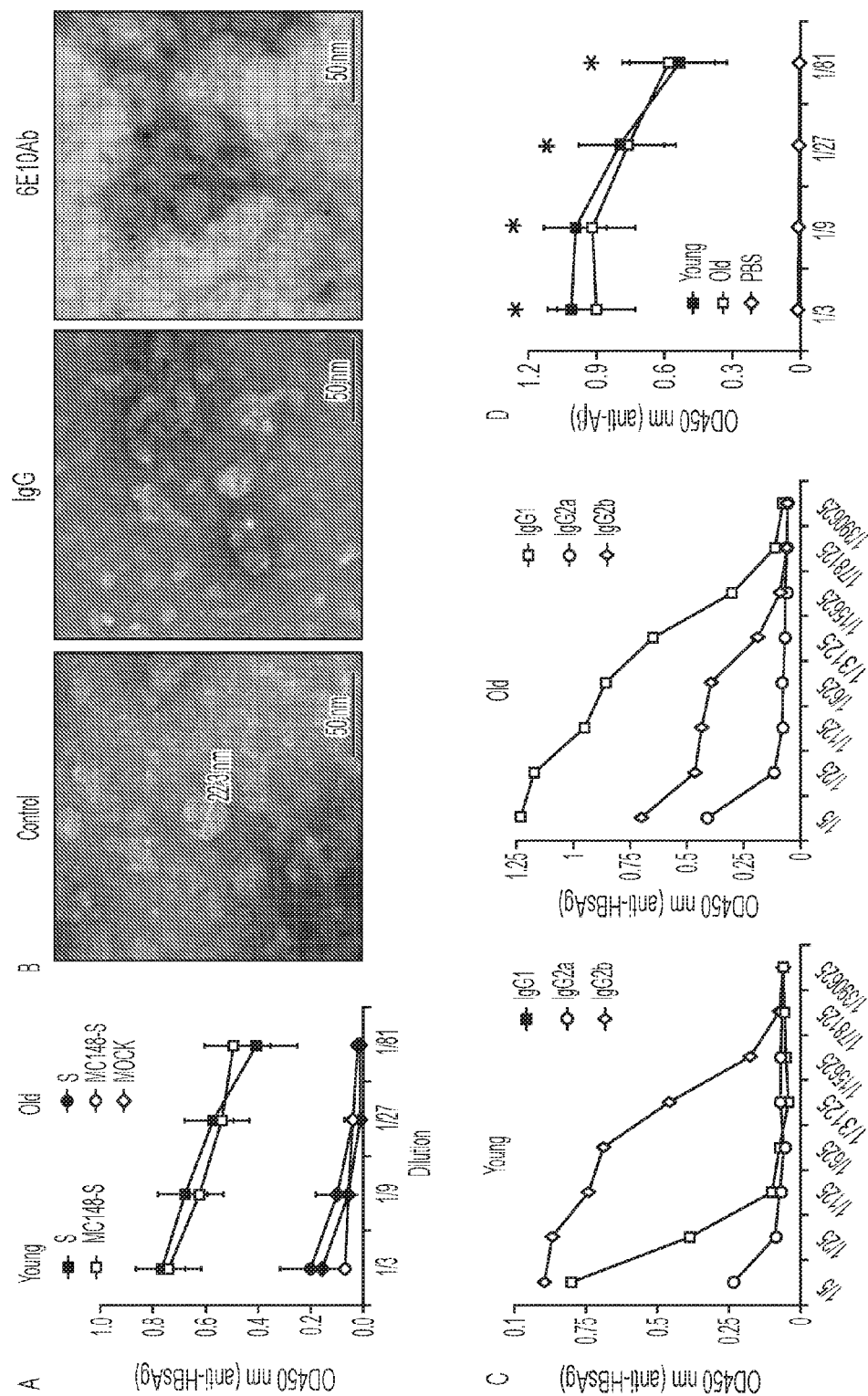
FIG. 1.

As described in the present disclosure, DNA immunizations with the amino-terminal Aβ(1-11) fragment exposed on the surface of HBsAg particles elicited high levels of anti-Aβ antibody both in young and old mice. Importantly, in AD model 3xTgAD mice (i.e., triple transgenic AD mice), the disclosed vaccine reduced Aβ plaques, ameliorated cognitive impairments and, surprisingly, significantly increased life span. Hence, disclosed vaccines comprising Aβ(1-11) efficiently combat AD-induced pathological alterations and provide survival benefit in patients with AD. Additionally, the vaccines described herein are responded to by older individuals, which usually respond poorly to vaccines in general, presumably due to age-related immunological impairments. This disclosure demonstrates that immunization of old AD mice with the vaccines described herein, early in the disease process, can not only improve AD-associated cognitive impairments, but also significantly extend life span. The disclosed vaccines may also provide survival benefits including increased life span in the absence of AD or a diagnosis of AD.

AD vaccines were developed according to the present disclosure, in which a DNA-based formulation was generated expressing Aβ(1-11) fused to HBsAg, which is a primary component of hepatitis B virus (HBV) vaccine. HBsAg was chosen based on its ability to self-assemble into 24 nm particles and to enhance immunogenicity of foreign antigens by repetitively exposing them on its surface. To enhance the activity of helper T cells, which are critical for an optimal B cell response to protein antigens, the construct also contained a strong T helper cell epitope from a capsid antigen of HBV (HBcAg).

The vaccine, designated Aβ-CoreS, generated high titers of antibody to Aβ both in young and old mice, while a control construct expressing HBsAg alone only worked well in young mice. Unlike mice immunized with a full-length Aβ(1-42) peptide that elicited readily detectable T cell responses, Aβ-CoreS-immunized mice failed to induce Aβ-specific T cells. Confirming that Aβ-specific T cell epitopes, which are present in longer Aβ peptides, are absent in the Aβ-CoreS vaccine of the present disclosure, Aβ-CoreS failed to elicit T cell response to Aβ in non-transgenic WT mice, which should not otherwise be hyporesponsive or affected by chronic Aβ exposure. Further, since no known human T cell epitopes are expressed in Aβ(1-11), the use of Aβ-CoreS in AD patients is expected to be safe.

The present disclosure demonstrates that Aβ-CoreS retains its efficacy when administered in relatively aged subjects early in the disease process (<15 months). The vaccine generated high levels of antibody in both young and old non-transgenic and 3xTgAD mice. As shown in the Examples, the immunized 3xTgAD mice exhibited reduced Aβ plaques in the hippocampus and improved performance in hippocampal-dependent contextual fear memory. The old age-associated antibody hypo-responsiveness is therefore reversible by administering strongly immunogenic vaccines like Aβ-CoreS.

Without being bound by a specific mechanism, the enhanced immunogenicity of Aβ-CoreS may be a result of the unique composition of the disclosed vaccine, specifically the presence of strong heterologous T helper epitopes of HBcAg and the use of empty self-assembled HBsAg particles that allows a repeated exposure of Aβ(1-11) on its surface. This is despite the fact that, unlike a prior chemokine-based Aβ vaccine which mostly induced IgG1 antibodies, the Aβ-CoreS-immunized 3xTgAD mice mostly exhibited IgG2b antibodies, an Fc-receptor low affinity binder that would be expected to be less effective in protecting against AD. Similar preferential IgG2b production was also observed when Aβ peptide was used with monophosphoryl lipid A adjuvant.

Without being bound to a specific mechanism, the IgG2b antibody may have cleared Aβ plaques in a similar fashion as F(ab)$_2$ antibody that solubilizes plaques without involving FcR binding. Aβ plaque solubilization was previously observed both in AD patients and transgenic AD mice, which was thought to be a cause of the redistribution of the Congophilic material to the vasculature and induction of a transient cerebral amyloid angiopathy.

As the present disclosure demonstrates, the Aβ vaccines described herein retain their potency in old mice, and produce therapeutic benefit when administered at a time point early in the disease process. Immunizations with Aβ-CoreS reduced Aβ plaques and enhanced cognitive functions in immunized 3xTgAD mice.

Dementia is associated with an enhanced mortality in humans, and thus premature death is associated with AD patients. However, long-term survival or clinical outcome in AD patients was not improved by immunization with a full-length Aβ(1-42) in a follow-up study of a phase I trial. By contrast, immunizations with the Aβ-CoreS vaccines described herein extended the survival of the 3xTgAD mice immunized. Note that the 20 month average life span of 3xTgAD mice is shorter than the average life span (25 months) of the background wild type strain (C57BL/6) of mice.

Although the mechanism of the survival benefit of the disclosed vaccine may be due to the inhibition of Aβ-associated pathologies or through the induction of antibody-mediated homeostasis of Aβ in the CNS, as in case of *Caenorhabditis elegans*, taken together, the disclosed data show that vaccines that target Aβ(1-11) can also be safely used in AD patients to promote extended survival by reducing Aβ-induced pathology and dementia. The vaccines may also extend life span in a mammal, including a human, who does not have AD or has not been diagnosed with AD.

The disclosed DNA vaccines were administered to mice using electroporation, as described further herein. See, e.g., Example 1. In another embodiment, the vaccines can be administered with an adjuvant, and may be formulated for targeting immature dendritic cells. For example, and without being bound by a specific mechanism, the effectiveness of some embodiments of the vaccine described herein is based on the ability of immature dendritic cells to manifest enhanced interaction with antigen, when the cells are exposed to an increased level of a chemokine such as MIP-3α. The MIP-3α binds to chemokine receptor CCR6 on the dendritic cell. The underlying concept of CCR6-mediated reactions to antigen by dendritic cells can be extended to other CCR6 ligands than MIP-3α, and ligands to other chemokine receptors on dendritic cells as described herein are suitable for achieving these purposes.

DNA encoding a fragment of the amyloid β protein can be used as antigen peptide for the vaccine construct. The fragment can be 6, 7, 8, 9, 10, 11, 12, 13, 14, 15, 16, 17, 18, 19, 20, 21, 22, 23, 24, 25, 26, 27, 28, 29, 30, 31, 32, 33 34, 35, 36, 37 38, 39, 40, or 41 amino acids of Aβ, and the antigen peptide can also be full-length Aβ. An exemplary amino acid sequence is provided as SEQ ID NO:1 (amino acids 1-11 of Aβ), but the vaccine is not limited to this sequence. Any length fragment of naturally occurring or synthetic Aβ, up to and including full length, is suitable for the vaccines disclosed herein, as long as it is capable of processing by an immature dendritic cell to yield an antigen portion that will elicit an immune response specific for the protein. The protein expressed by the DNA vaccine is taken up by immature dendritic cells, where it is processed into antigenic components.

Effective variants of the sequences disclosed herein can also be used. Variants include polynucleotides encoding peptides having one or more conservative amino acid substitutions. As used herein, a "conservative substitution"

involves a substitution of one amino acid for another found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company which is incorporated by reference for its teachings regarding the same.

Variants also include peptide and nucleotide sequences with at least 70% sequence identity, 80% sequence identity, 85% sequence, 90% sequence identity, 95% sequence identity, 96% sequence identity, 97% sequence identity, 98% sequence identity, or 99% sequence identity to any of the polypeptide or nucleotide sequences disclosed herein.

"% identity" refers to a relationship between two or more protein sequences, as determined by comparing the sequences. In the art, "identity" also means the degree of sequence relatedness between proteins as determined by the match between strings of such sequences. "Identity" (often referred to as "similarity") can be readily calculated by known methods, including (but not limited to) those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992), each incorporated by reference herein for its teachings regarding the same. Preferred methods to determine identity are designed to give the best match between the sequences tested. Methods to determine identity and similarity are codified in publicly available computer programs. Sequence alignments and percent identity calculations may be performed using the Megalign program of the Lasergene bioinformatics computing suite (DNASTAR®, Inc., Madison, Wis.). Multiple alignment of the sequences can also be performed using the Clustal method of alignment (Higgins and Sharp CABIOS, 5, 151-153 (1989), incorporated by reference herein for its teaching regarding the same) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990), incorporated by reference herein for its teaching regarding the same); DNASTAR®; and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. incorporated by reference herein for its teaching regarding the same). Within the context of this disclosure it will be understood that where sequence analysis software is used for analysis, the results of the analysis are based on the "default values" of the program referenced. As used herein "default values" will mean any set of values or parameters which originally load with the software when first initialized.

The vaccine can be administered as a protein or polypeptide encoded by the DNA construct, in combination with an adjuvant. The protein or polypeptide of the vaccine can comprise a ligand for a dendritic cell chemokine receptor, fused to an antigen. The ligand can be a chemokine, including MIP-3α, and the antigen can be a fragment of Aβ, in particular amino acids 1-11 of Aβ, and the adjuvant can be VAXFECTIN®.

The protein or polypeptide can be expressed using any method known in the art, including but not limited to expression in a mammalian cell, a bacterial cell, a yeast cell, an insect cell, or in a cell-free system. An exemplary plasmid for protein expression is plasmid VR1012 into which can be inserted the DNA comprising (i) a polynucleotide sequence encoding an antigenic Aβ polypeptide; (ii) a polynucleotide sequence encoding T-helper epitope of hepatitis B virus capsid antigen; and, (iii) a polynucleotide sequence of the S gene of hepatitis B virus, wherein the antigenic peptide can comprise the polypeptide of SEQ ID NO:1. Plasmid VR1012 is described in, for example, Hartikka, J., et al., Hum. Gene Ther. 7: 1205-1217, 1996, which is incorporated herein by reference in its entirety.

In certain embodiments, the polynucleotide sequence of the T-helper epitope of hepatitis B virus capsid antigen comprises the nucleotide sequence of SEQ ID NO:2.

A vaccine for alleviating Alzheimer's Disease elicits and/or boosts a host antibody response, wherein the response recognizes Aβ proteins in the host's tissues. Achieving any antibody response involves a series of immune cells and activities. Dendritic cells play an important role in the development and activity of antibody-secreting cells, and in some embodiments the vaccines disclosed herein act by targeting dendritic cells for maturation.

Dendritic Cells.

Dendritic cells are referred to herein and in the art as DCs, and in immature form, as iDCs. DCs are among the family of antigen-presenting cells, and act as both initiators and modulators of the immune response to, in this case, antigens from pathogenic and infectious agents. DCs are also referred to as Langerhans cells when present in the skin. Although DCs play an important role in presenting antigen to T lymphocytes and thereby initiating T-cell immune reactions including inducing B-cell growth and antibody production, in the present disclosure a main focus is on the role of DCs in B lymphocyte reaction to antigen. Without being bound by a specific mechanism, the methods herein can employ DCs that are active in this setting by enhancing the activity of helper T cells, which in turn enhance the antibody responses.

During the maturation from iDC to DC, the expression of chemokine receptors on the cell surface changes. The iDCs have been reported to express CXCR2, CXCR4, CCR1, CCR2, CCR3, CCR4, CCR5, CCR6, CCR7, and CCR8, although at varying levels. Mature DCs lose the expression of most of these receptors, and gain expression of CXCR4, CXCR5, plus enhanced expression of CCR7.

Although these are referred to as "chemokine" receptors, other ligands are capable of binding these receptors than chemokines per se. For example, the CCR6 receptor also interacts with human β-defensins, as demonstrated by the ability of β-defensin to displace a chemokine ligand for CCR6. Suitable β-defensins include but are not limited to natural, recombinant, and synthetic forms of human β-defensin 1 and human β-defensin 2, which possess chemotactic activity towards iDCs. Portions of these β-defensins that retain the ability to bind to an iDC receptor, including but not limited to CCR6, are also suitable for use in the disclosed DNA vaccines. It is routine in the art to prepare a fragment or portion of a β-defensin protein and measure chemotactic activity towards iDCs using, for example, methods described in Yang, D. et al., Science 286:525-528, 1999, which is incorporated herein by reference in its entirety. Other suitable defensins and defensin-like proteins are disclosed in Biragyn, A. et al., Blood 100:1153-1159 (2002) and in Biragyn, A. et al., J. Immunol. 167:6644-6653 (2001), which are also incorporated herein by reference in their entirety.

In the context of the disclosed vaccines, then, any protein that can specifically compete with a CCR6 ligand, particularly that competes with MIP-3α or β-defensin 1 or 2, is suitable to achieve the goal of enhancing the iDC response to antigen. Examples of such competing proteins are any of the monocyte chemotactic proteins (MCP). Accordingly, DNA which encodes such a protein can be linked to the DNA encoding the antigen for use in the vaccines of the present disclosure.

B cells differentiate and produce antibody in response to DC stimulation. B cells can also be activated by direct exposure to antigen. DCs may contribute to the development of helper T cells, which are critical for an optimal B cell response to protein antigens. DCs also stimulate the production of antibodies through the secretion of soluble factors including IL-12. It is estimated that the human skin contains about $10^9$ skin dendritic cells, known as Langerhans cells. After activation by antigen, such as by the disclosed vaccines, these DCs migrate to the spleen, lymph node, and other lymphoid tissues. Here they continue maturation, and attract B cells through release of chemokines. After the initial antigen intake, the DCs lose their endocytotic ability, thereby retaining only antigens specific for the original site of infection or vaccination.

Among their many immune activities that support the immune reaction to a specific infectious agent, as represented by the antigen(s) that first stimulated the immune response, DCs express receptors for complement and Fc, thereby capturing and displaying antigen-antibody complexes. This contributes to the sustained proliferation of, and antibody production by, B cells.

Chemokines.

Without being bound by a specific mechanism, the DNA vaccines of the present disclosure act with enhanced efficacy compared to antigen alone, for example by providing a chemokine to create a more effective interaction between iDC's and antigen. Inclusion of DNA encoding an immune cell product, such as a chemokine, accomplishes the targeting of receptors on immature dendritic cells as discussed above, thereby recruiting them in an Aβ antigen-specific manner.

Prior to exposure to a specific antigen, dendritic cells exist as immature cells in tissues, and possess high capacity to phagocytize. These immature dendritic cells express an array of receptors through which corresponding chemokines enter the cell. By associating a chemokine with an Aβ antigen in the construct of this disclosure, the immature dendritic cells perform the activation and antigen capture process more efficiently than if the two elements are presented separately.

Without being bound by a specific mechanism, the data suggest that the DNA vaccines disclosed herein may function by first introducing DNA encoding a chemokine and an antigen into cells at or near the vaccination site, including but not limited to, muscle cells. These cells express the linked chemokine-antigen protein into the extracellular environment, and the chemokine binds to its corresponding receptor on immature dendritic cells. The chemokine and antigen are taken into the cell, where the antigen is processed to begin the process of dendritic cell maturation and migration and antigen presentation to T cells and B cells.

The DNA encoding a chemokine can be selected on the basis of the receptors present on the immature dendritic cells and the intended result. One CCR6 receptor ligand is macrophage inflammatory protein 3α (MIP-3α). The vaccine constructs as described herein are not limited to use of the particular CCR6 ligand MIP-3α, however. Instead, the goal of the vaccines described herein is to engage antigen presenting cells (dendritic cells) and enhance the efficiency of antigen engagement by these cells, compared to use of the antigen alone. Thus, other possible CCR6 ligands include, without limitation, b-defensins and monocyte chemotactic proteins as discussed above.

Additional chemokines suitable for the DNA vaccine, either full-length or as functional fragments, include those in the C—C family, including monocyte chemotactic proteins (MCP) 1, 2, and 3; macrophage inflammatory proteins (MIP) 1α and 1β; and RANTES (CCL5). These proteins are chemotactic for DCs. Members of the C—X—C chemokine family for which DCs have receptors include IL-8 and neutrophil-activating peptide-2 (NAP2, or CXCL7).

These and some examples, without limitation, of other suitable dendritic cell receptors and ligands are shown in Table 1.

TABLE 1

| Dendritic cell receptor | Ligand |
| --- | --- |
| CCR6 | MIP-3α |
|  | Human β-defensin 1 |
|  | Human β-defensin 2 |
|  | Monocyte chemotactic proteins |
| CCR1 | MIP-1α |
|  | MIP-5 |
|  | CCL5/RANTES |
|  | MCP-2 |
|  | MCP-3 |
|  | MPIF-1 |
| CCR2 | MCP-1 |
|  | MCP-4 |
| CCR3 | Eotaxin, Eotaxin-2 and 3 |
|  | CCL5/RANTES |
|  | MCP-1 |
|  | MCP-3 |
|  | MCP-4 |
|  | MEK |
|  | MIP-5 |
|  | LPS-iCK |
| CCR4 | MIP-1α |
|  | CCL22 |
| CCR5 | MIP-1α |
|  | MIP-1β |
|  | CCL5/RANTES |
|  | MCP-2 |

TABLE 1-continued

| Dendritic cell receptor | Ligand |
| --- | --- |
| CCR7 | CCL-19 |
| | CCL-21 |
| CCR8 | CCL-1 |
| CXCR1 | IL-8 |
| CXCR2 | CXCL1 |
| | Epithelial-derived neutrophil-activating peptide-78; |
| | Granulocyte chemotactic protein; |
| | Neutrophil-activating peptide 2; |
| | Lipopolysaccharide-induced CXC chemokine |
| CXCR3 | CXCL9 |
| | CXCL10 |
| | CXCL11 |

Two components of the vaccines of the present disclosure, i.e. the Aβ protein and the dendritic cell chemokine receptor ligand, are discussed above. To further achieve an effective vaccine according to this disclosure, materials and methods are employed to enhance expression of the DNA vaccine and/or to enhance availability of the vaccine for iDC processing. One example of such a method employs an adjuvant, and another example employs electroporation. Both are discussed below.

Adjuvants.

The term "adjuvant" refers to material that enhances the immune response to an antigen and is used herein in the customary use of the term. The precise mode of action is not the same for all adjuvants, nor indeed is it understood for all adjuvants. However, such lack of understanding does not prevent their clinical use for a wide variety of vaccines, whether protein-based or DNA-based. Traditionally, some adjuvants physically trap antigen at the site of injection, thereby enhancing antigen presence at the site and slowing its release. This in turn prolongs and/or increases the recruitment and activation of antigen presenting cells (APCs), such as in this case immature dendritic cells.

Without being bound by a specific mechanism, the use of liposome adjuvants in the present vaccine formulation may also facilitate sustained antigen loading of local DCs. Thus, adjuvants suitable for use herein include liposome formulations as taught by Schwendener, R. A. et al., Methods Mol. Biol. 605:163-75 (2010), which is incorporated herein by reference in its entirety. In Schwendener, intradermal injection of plasmid-DNA liposomes encoding the gp33 glycoprotein of the lymphocytic choriomeningitis virus (LCMV) formed LCMV "antigen depots," and these antigen depots enabled long-lasting antigen loading of DCs in vivo, and was associated with a strong immune response.

One example of an adjuvant suitable for the disclosed Aβ vaccines is VAXFECTIN® (Vical Inc., San Diego, Calif.), a cationic lipid-based formulation. The adjuvant is a commixture of a cationic lipid and a neutral phospholipid in an aqueous vehicle, allowing the self-assembling of the components into liposomes. When mixed with a vaccine, the cationic liposomes associate with the vaccine via charge-based interactions. VAXFECTIN® is described in, for example, Hartikka, J. et al., Vaccine 19:1911-1923 (2001), which is incorporated herein by reference in its entirety.

Electroporation for Tissue Delivery of DNA Vaccine.

DNA immunization with the vaccines as disclosed herein can be accomplished by, for example, electroporation for delivery of vaccine polynucleotides into cells. The methods herein are not limited to a specific system or manufacturer, and one of skill in the art will be familiar with systems and apparatuses available. An exemplary method is described herein, and methods are also described in Example 1. As an example, an in vivo electroporation system, termed EASY VAX™ (Cellectis Therapeutics, Paris, France), as originally developed by Cyto Pulse Sciences (Baltimore, Md.), can be used. This vaccine delivery system is designed to deliver large molecules, using pulsed electric fields, in vivo directly into human skin cells to elicit an immune response against a specific target. The delivery system includes a single-use microneedle array in which each needle is coated with the polynucleotide of the vaccine. There are hundreds of microneedles in the array aligned in 20 or more rows, with each row of needles dielectrically isolated. The array is a few millimeters square and the needles are <1 mm long.

Typically, when inserted into the skin, there are approximately 6200 epithelial cells and 25 Langerhans cells (including dendritic cells) within the volume between any two rows when inserted 0.15 mm. The system also includes a Waveform Generator that applies a pulsed voltage (1-50 volts) from one row of needles to the next. The electric field established between the needle rows permeabilizes the membranes of the cells between the rows permitting the polynucleotides to enter the cells.

This system includes several design features that enhance immunization. First, the electrode needles are only 150-500µ long, ensuring that the majority of the needles do not penetrate significantly beyond the basal lamina of the skin. Second, the needles are spaced very close together, reducing the absolute voltage required to achieve cell membrane permeabilization. These design features result in a painless delivery system and places the DNA at a site of abundant Langerhans cells to engage the proteins secreted by the cells that take up the DNA.

The results of an experiment comparing immunization with vaccinia DNA using the Easy Vax system vs. immunization using the standard scarification technique with live vaccinia demonstrated that equivalent ELISA and neutralization titers were obtained with either method. Additionally, previous studies indicate a dramatic enhancement of the response to DNA encoding HBsAg when electroporation using the EASY VAX™ system is added to the immunization regimen.

In the present disclosure, electroporation as described above can be used with the Aβ DNA vaccine constructs. As described above for the DNA vaccine construct administered with adjuvant, the mechanism involves uptake of DNA by cells at the site of administration, expression of the chemokine-antigen protein, and association of the chemokine with corresponding receptor on immature dendritic cells in the vicinity of the vaccination.

Without being bound by a specific mechanism, the VAXFECTIN® can be employed to bring more dendritic cells to the site of inflammation, in this case due to vaccination. As a result, more dendritic cells are available for binding to the Aβ protein secreted by muscle cells, among other cells that have taken up the DNA. Electroporation, by contrast, likely increases the uptake by the muscle cells and other cells in the vicinity of the vaccination, effectively making more protein available for binding to dendritic cells. Electroporation therefore may not depend on increasing the number of dendritic cells in the site of vaccination. Both methods (adjuvant and electroporation) achieve the goal of increasing the efficiency of interaction between the vaccine protein and the available dendritic cells: adjuvant achieves this by increasing the dendritic cell numbers in the environment, and electroporation achieves this by increasing vaccine protein in the environment.

The vaccine can be administered as a protein or polypeptide encoded by the DNA construct, in combination with an adjuvant. The protein or polypeptide of the vaccine can comprise a ligand for a dendritic cell chemokine receptor, fused to an antigen. The ligand can be a chemokine, including MIP-3α, and the antigen can be a fragment of amyloid β-peptide, in particular amino acids 1-11 of Aβ, and the adjuvant can be VAXFECTIN®.

The protein or polypeptide can be expressed using any method known in the art, including but not limited to expression in a mammalian cell, a bacterial cell, a yeast cell, an insect cell, or in a cell-free system.

In other embodiments, the DNA vaccines disclosed herein are produced in bacterial systems known to persons of ordinary skill in the art.

The DNA vaccines, or proteins expressed by the DNA vaccines, are administered to humans in need thereof either before the onset of Alzheimer's Disease symptoms, in individuals known to be at risk of Alzheimer's Disease, or in humans already diagnosed with Alzheimer's Disease. Individuals known to be at risk for development of Alzheimer's Disease include those over 65 years of age, individuals with a family history (a parent, brother, sister, and/or child) with Alzheimer's disease, or those with a genetic risk of the disease such as having the ApoE4 gene or known increased risk variants of amyloid precursor protein, presenilin-1, and/or presenilin-2.

Alzheimer's disease is diagnosed by a combination of medical history, mental status testing, physical and neurological examination, and blood and brain imaging testing.

As used herein, "treating" Alzheimer's disease refers to decreasing or preventing behavioral, functional, and cognitive deterioration over time. Behavioral, functional, and cognitive aspects of Alzheimer's Disease are evaluated by a series of standardized tests known to persons of ordinary skill in the art including, but not limited to, neuropsychological testing, the Mini-Mental State Exam, Mini-cog exam, Neuropsychiatric Inventory, Blessed Roth Dementia Rating Scale, Spanish and English Neuropsychological Assessment Scales (SENAS), Psychiatric Behavioral Assessment, Functional Assessment, Clock Drawing Test, Boston Naming Test, California Verbal Learning Test, Cognitive Symptoms Checklist, Continuous Performance Test, Controlled Oral Word Association Test, Cognistat, d2 Test of Attention, Delis-Kaplan Executive Function System, Dementia Rating Scale, Digit Vigilance Test, Figural Fluency Test, Finger Tapping Test, Halstead Category Test, Halstead-Reitan Neuropsychological Battery, Hooper Visual Organization Test, Kaplan Baycrest Neurocognitive Assessment, Kaufman Short Neuropsychological Assessment, Luria-Nebraska Neuropsychological Battery, Memory Assessment Scales, Quick Neurological Screening Test, Repeatable Battery for the Assessment of Neuropsychological Status, Stroop Test, Symbol Digit Modalities Test, Tactual Performance Test, Thematic Apperception Test, Tower of London, Trail Making Tests A and B, Verbal (Word) Fluency Tests, and Wisconsin Card Sort Test. Additional tests for depression, anxiety, aphasia, agitation, and behavioral parameters known to persons of ordinary skill in the art are also used. Periodic use of one or more of these tests can advise a physician or other medical professional as to the progression, or regression of Alzheimer's Disease and the need to further treatment. The choice of test and the determination of success of treatment is within the expertise of medical professionals in the Alzheimer's Disease field. An improved score in one or more tests is an indication of decrease in severity of the Alzheimer's Disease.

It is anticipated that the vaccines disclosed herein will be administered in a plurality of administrations such as daily, weekly, biweekly, bimonthly, monthly, every other month, every third month, etc. In certain embodiments, a vaccine holiday may be taken in which the vaccination schedule is interrupted for a planned period of time and then resumed.

Effectiveness of a vaccine disclosed herein can be determined by generation of antibodies, reactive T cells, or other specific immune responses to the vaccine components. In one embodiment, the effectiveness of a vaccine disclosed herein is determined by measuring the titer of antibodies to Aβ. Methods of determination of antibody titers are known to persons of ordinary skill in the art. Persons skilled in the art, such as medical professionals, can determine if the antibody titers after vaccination indicate that additional vaccinations are necessary, or if the previously conducted vaccinations were sufficient.

The Examples below are included to demonstrate various embodiments of the disclosure. It should be appreciated by those of ordinary skill in the art that the techniques disclosed in the Examples represent techniques and compositions discovered by the inventor to function well in the practice of the disclosure, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the disclosure.

EXAMPLES

In the Examples below, the following reagents, cells, DNA constructs, and mice were used. BALB/C and C57BL/6 mice were obtained from The Jackson Laboratory (Bar Harbor, Me.). Triple transgenic AD (3xTgAD) mice were originally generated in a hybrid 129/C57BL/6 genetic background (see Oddo, S. et al., Neuron 39:409-421, 2003, which is incorporated herein by reference in its entirety), and were then backcrossed onto a pure C57BL/6 genetic background for eight generations. Aβ and tau pathologies and learning and memory deficits in these mice have been reported. All mice were bred and housed in a pathogen-free environment.

DNA fragments encoding the T helper epitope of HBcAg (residues 70-85) and Aβ(1-11) were fused in-frame with the S gene of HBV (HBsAg, subtype ayw) and cloned into a mammalian pVAX1 vector (Life Technologies (Invitrogen), Grand Island, N.Y.). Control constructs expressed HBsAg alone (S) or HBsAg fused with MC148 of the poxvirus *Molluscum contagiosum*. All constructs were verified by DNA sequencing.

The peptides mouse-gp100(25-33) (EGSRNQDWL; SEQ ID NO:5) and MOPC-315 Ig (91-101) (ALWFRNHFVF-GGGTK; SEQ ID NO:6) were synthesized by Peptide Technologies (Washington, D.C.) to a purity>99% by HPLC. Aβ(1-42) was obtained from Bachem (Torrance, Calif.).

Statistical Analysis.

Results are presented as the mean of triplicates±SEM of at least three experiments. Differences were tested using Student's t test, and a 2 sided p-value less than 0.05 was considered statistically significant.

Example 1

Aβ-CoreS is a Potent Immunogen in Young and Old Mice

This Example was performed to test whether vaccination at onset of AD can be effective. As background, prior to the present disclosure it remained poorly understood whether AD could be combated by vaccine administration at the onset of the disease, as vaccines can lose their efficacy due to tolerance to Aβ and old age-associated immunological impairments.

In Vivo Manipulations.

Three different groups of mice were immunized three or four times (as indicated for specific experiments) every two weeks starting when mice were 4 months old (young mice), 1 year old, or 1.5 years old. To do this, mice were electroporated with 25 µg DNA in 50 µl endotoxin-free water intradermally in the base of the tail using a parallel row needle array (with two rows of four needles/row, a 1 mm gap between needles within a row, a 4 mm gap between rows and a needle length of 3 mm) connected to a PA-4000 electroporation system (Cyto Pulse Sciences, Inc., Glen Burnie, Md.).

A Pulse AgileR electroporation protocol was used, consisting of two pulses of 450 V (1125 V/cm), 0.125 S pulse interval and 0.05 mS pulse duration followed by eight pulses of 110 V (275 V/cm) at 0.125 S pulse interval and 10 mS pulse duration. Control mice were subcutaneously immunized with 10 µg Aβ(1-42) (or mock with 100 µl PBS) emulsified in 100 µl incomplete Freund's adjuvant (IFA) or coupled with alum (Sigma). Date of death was recorded and differences in survival between groups were determined by non-parametric logrank test (BMDP statistical software, Los Angeles, Calif.).

Mice of various ages ranging from 8 weeks old (young) to 15 months old were DNA immunized. As shown in FIG. 1A, while three immunizations with HBsAg-expressing DNA vaccine generated significant humoral responses in 8 week-old mice, practically no vaccine-specific (anti-S) antibody was detected in 15 month-old C57BL/6 mice in side-by-side experiments.

Additional experiments indicated that the vaccine lost efficacy starting from 12 months of age regardless of the mouse strain used (BALB/C, C57BL/6 and AKR/J mice). The immunogenicity of HBsAg was not improved in old mice even after fusing it with a viral antigen MC148 (MC148-S, FIG. 1A), a strategy shown to be effective for the generation of anti-tumor immune responses. Comparable anti-HBsAg antibody can be induced in old mice after five or more immunizations, thus indicating, as in older humans, that older mice respond poorly to vaccines. The present Example, however, demonstrates that this issue was overcome by the vaccines of the present disclosure, as described below.

To develop an AD vaccine that circumvents poor vaccine response in old age, a chimeric HBsAg gene expressing Aβ(1-11) fragment and a strong Th epitope of capsid antigen of HBV (Milich, D. R. et al., J. Virol. 69:2776-2785, 1995) were generated. The resulting construct, designated Aβ-CoreS, formed 24-36 nm particles with Aβ(1-11) exposed on their surface, as revealed by ELISA and electron microscopy immune-gold analysis using 6E10 antibody that recognizes the amino-terminus of Aβ (FIG. 1B). Unlike the HBsAg vaccine (FIG. 1A), immunizations with Aβ-CoreS generated high and comparable levels of antibody to HBsAg in young and 15 month-old C57BL/6 mice (FIG. 1C), indicating that the age-associated poor humoral responses can be reversed by the vaccines of the present disclosure.

Figure 2:
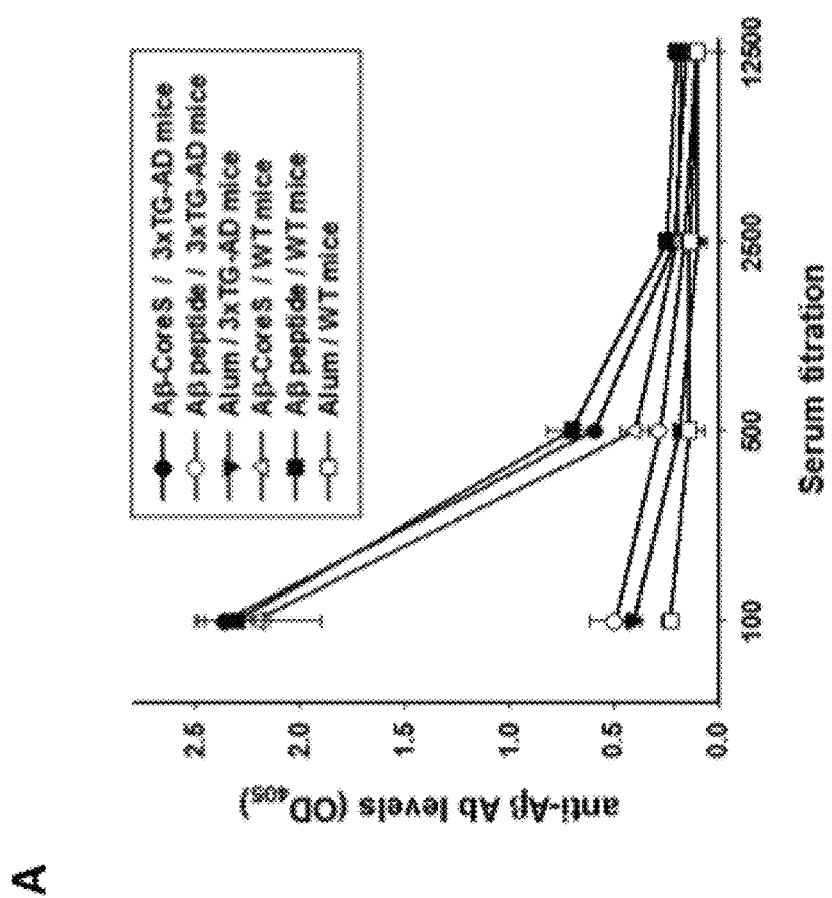
FIG. 2.
Figure 2:
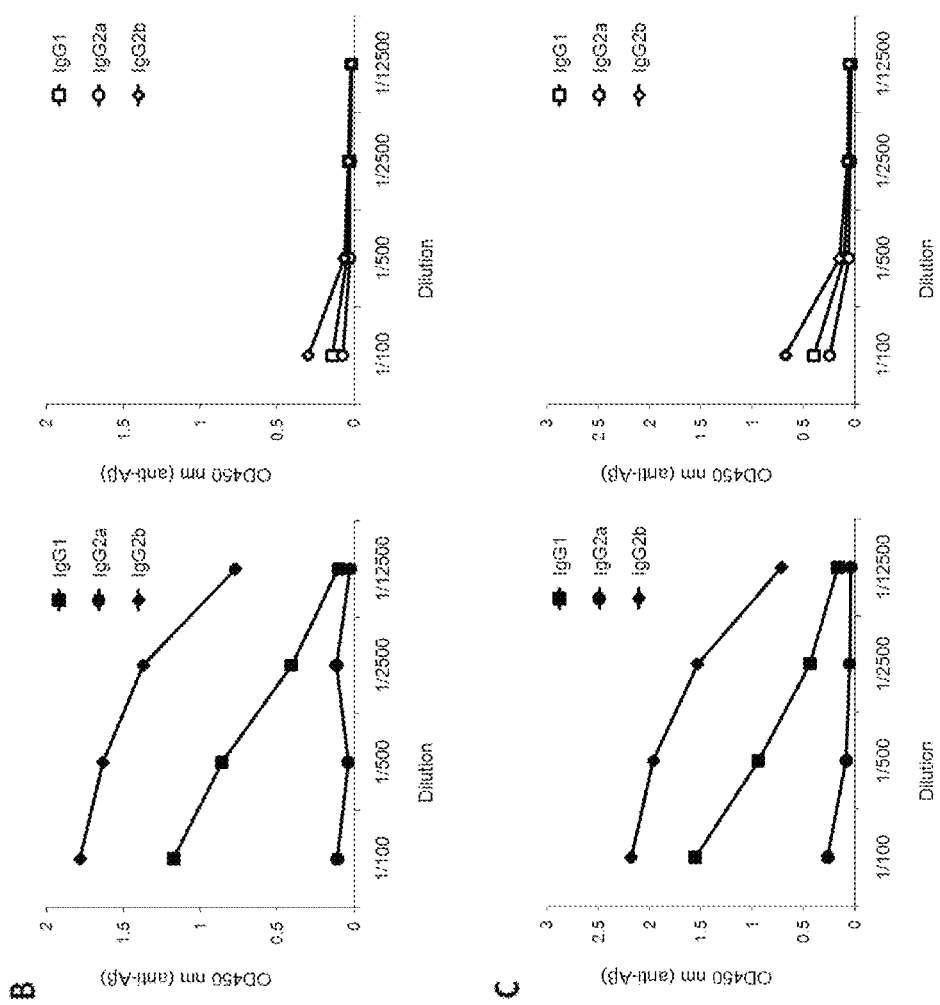

Importantly, the Aβ-CoreS vaccine also generated comparable levels of anti-Aβ antibody in both ages of WT C57BL/6 (FIG. 1D) and 3xTgAD (FIG. 2A) mice. Aβ-CoreS generated Aβ-specific antibody predominantly represented by IgG2b (titers>1:6000 after three immunizations) and to a lesser degree IgG1, without detectable IgG2a or IgG3 (FIG. 2B, C). Moreover, confirming a report on the inability of Aβ(1-42) peptide immunizations to overcome tolerance to Aβ, immunizations with Aβ(1-42) peptide failed to generate Aβ-specific antibody in 12-month old 3xTgAD mice in side-by-side experiments regardless of adjuvant use (Alum, FIG. 2A; and IFA). Hence, despite the issues related to old age and potential Aβ tolerance, the Aβ-CoreS vaccines of this disclosure induced potent anti-Aβ humoral responses in 3xTgAD mice.

Example 2

T Cell Activation Assay

To assess T cell proliferation, splenocytes from immunized and mock-treated mice were first labeled with carboxyfluorescein succinimidyl ester (CFSE, Invitrogen, Carlsbad, Calif.). The cells then were stimulated with either 1 µg/ml of Aβ(1-42) or 10 µg/ml of HBsAg (#R86870, Biodesign, Saco, Me.) in RPMI1640 medium containing 10% fetal bovine serum and antibiotics and 50 U/ml of IL-2. Control CFSE-labeled cells ($1\times10^5$) were stimulated with anti-CD3/CD28-coupled beads or mouse-gp100$_{25-33}$ (EGSRNQDWL; SEQ ID NO:5).

After 7 days incubation, the cells were stained with anti-CD4 and anti-CD8 antibodies (BD Biosciences Pharmingen, San Jose, Calif.) to quantify the proportion (%) of proliferated (CFSE-diluted) cells which was calculated as: (Experimental−target spontaneous)/(target maximum after anti-CD3/CD28 Aβ treatment−target spontaneous)× 100.

For 3xTgAD splenocytes, the cells were also re-stimulated for another 7 days with irradiated autologous bone marrow-derived dendritic cells (BMDCs) and pulsed with 1 µg/ml Aβ(1-42) peptide or HBsAg. Serum levels of antibody to Aβ and HBsAg were measured in 96-well ELISA plates coated with 3 µg/ml Aβ(1-42) or HBsAg (ayw, Biodesign) using goat anti-mouse IgG-HRPO (Jackson ImmunoResearch, West Grove, Pa.).

The results showed that Aβ-CoreS did not induce T cell responses to Aβ. WT (C57BL/6) mice were DNA immunized with Aβ-CoreS or with a full-length Aβ(1-42) peptide emulsified in IFA. Ten days after the third immunization, splenic T cells were ex vivo labeled with CFSE and stimulated with antigen-presenting cells (APCs) and pulsed for five days with Aβ(1-42) or control (irrelevant peptide) (Mock). The cells were then stained with anti-CD4 and CD8 antibodies to quantify the proportion of CD4$^+$ and CD8$^+$ T cells that diluted CFSE (proliferated T cells).

Figure 3:
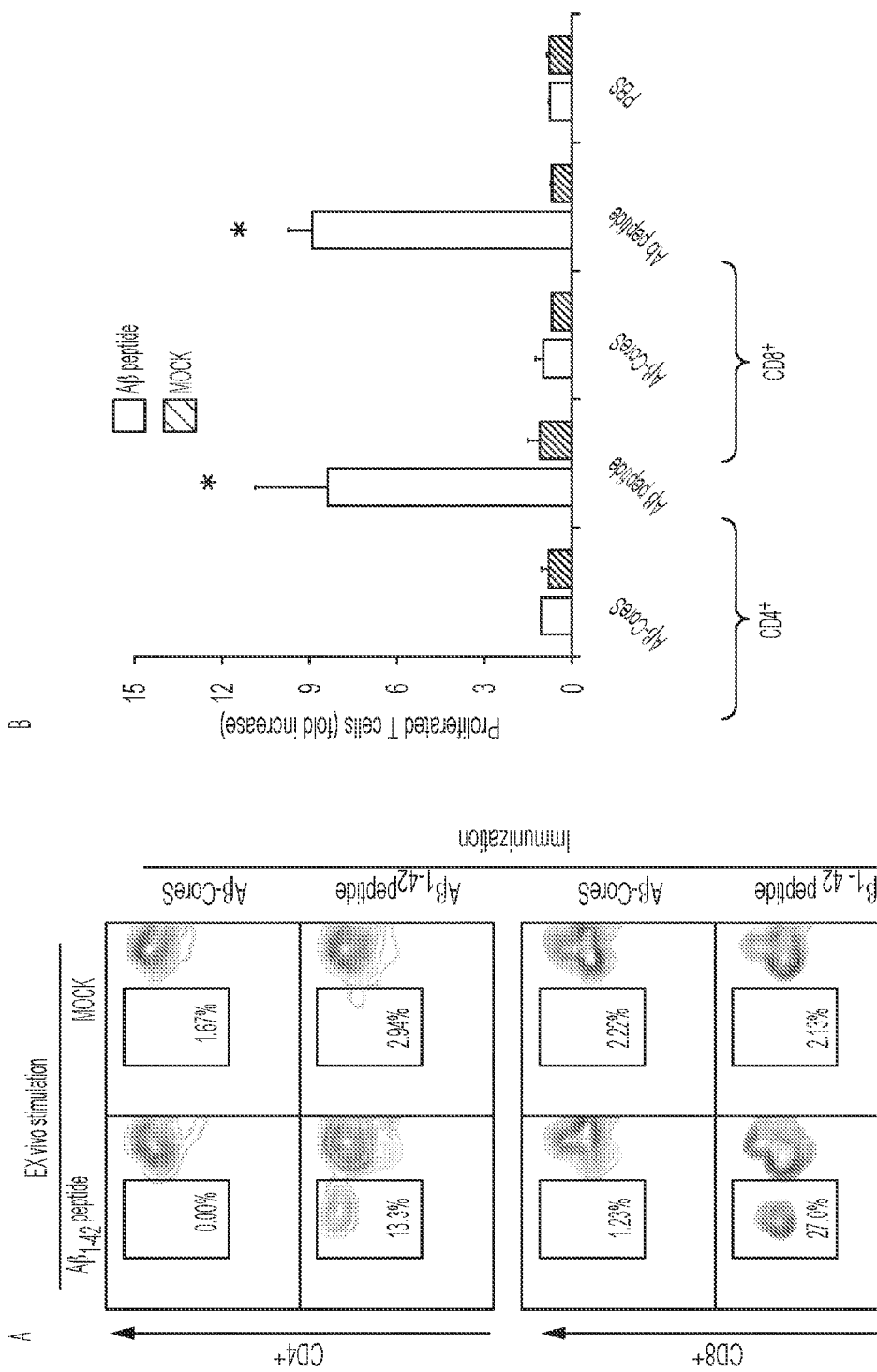
FIG. 3.
Figure 3:
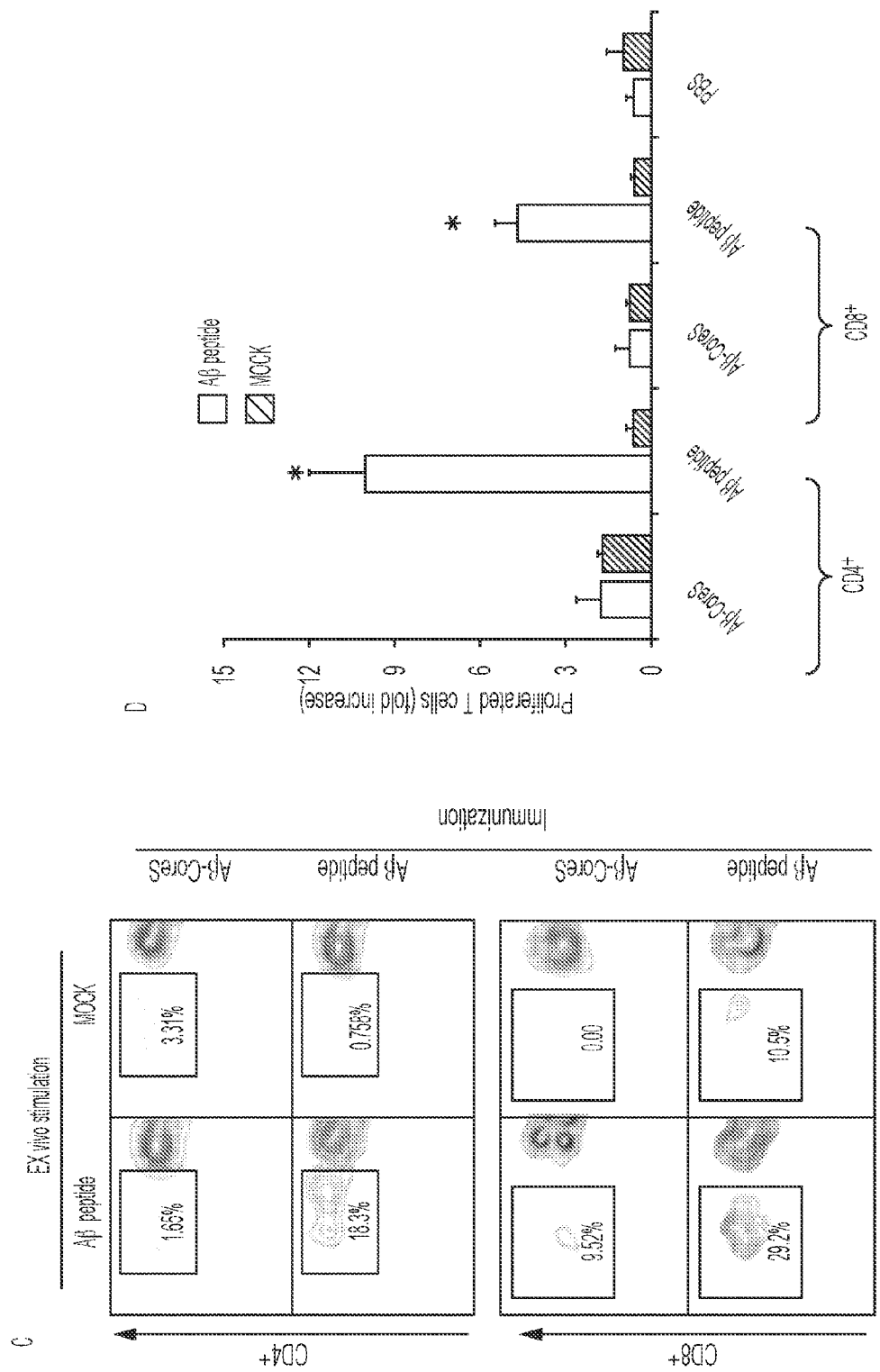

While both CD4$^+$ and CD8$^+$ T cells from mice immunized with full-length Aβ (1-42) readily proliferated (FIG. 3A, 3B), Aβ-specific T cell activity was not detected in splenocytes from Aβ-CoreS-immunized mice (FIG. 3A, 3B). As in young mice (FIG. 3A, 3B), Aβ-CoreS immunizations of old mice also did not activate Aβ-specific CD4$^+$ and CD8$^+$ T cells (FIG. 3C, 3D). Aβ-CoreS did not elicit Aβ-specific T cell responses even if the immunizations started at a young age (8 weeks old) and then the mice were booster-immunized at 12 months.

This lack of T cell activity was not due to the inability of mice to recognize Aβ, as significant T cell proliferation was detected in young and old mice immunized with Aβ(1-42) peptide (FIG. 3B, 3D). Thus, the results herein show that Aβ-CoreS cannot induce T cell responses in WT mice despite the generation of antibody responses to Aβ (FIG. 1D). Similarly, immunizations with Aβ-CoreS also failed to induce proliferation of T cells from 3xTgAD mice, although a high rate of spontaneous proliferation of T cells from mock-treated 3xTgAD mice did not allow this to be quantified. Taken together, the Aβ-CoreS formulation predominantly generates anti-Aβ antibody without eliciting Aβ-specific cellular responses. Example 3. Aβ-CoreS vaccine reduced Aβ plaques, improved cognition and extended survival of 3xTgAD mice.

Several parameters were tested to evaluate the effect of the Aβ-CoreS vaccines on mice.

Elevated Plus Maze Test.

The elevated plus maze test was conducted under a controlled light intensity of 1,300 lux. The apparatus consisted of a plus-shaped maze elevated 60 cm from the floor. Two open arms, each 25 cm×5 cm with a 1 cm high edge, were crossed by two arms of the same dimensions, but enclosed by 30 cm high walls.

Each animal was placed in the middle of the maze, facing an open arm, and allowed to explore the apparatus for 5 min. Following testing, mice were returned to their home cages and the apparatus was cleaned with 70% ethanol to remove any odor cues. Activity was monitored and analyzed using ANY-maze tracking software (Stoeltling Co., Wood Dale, Ill.). Entrance to an arm was considered when all four paws entered the arm.

Fear Conditioning.

Fear conditioning tests were conducted in sound attenuating boxes (model ENV-022V; Med Associates, Inc., St. Albans, Vt.). During the training session, mice were placed in a contextual conditioning chamber (model MED-VFC-NIR-M; Med Associates) and baseline freezing activity was recorded for 2 minutes. After 2 minutes, mice were subjected to 3 pairings of audio tones and foot shocks, each separated by thirty seconds without stimuli for a total of 5 minutes. Each 30 second audio tone (5 kHz, 70 dB) was immediately followed by a 2 second foot shock (0.5 mA) from an exposed electrified metal floor grid. The percent time spent freezing was used as a measure of the strength of the conditioned response.

Following training (as well as following the next phases of this test as described below) mice were returned to their home cages and all equipment was cleaned with water and 70% ethanol to remove any odor cues. The next day, the mice were returned to the testing chamber for the contextual fear session. Activity in the chamber was monitored for 5 minutes without any tones or shock. The percentage of time spent freezing was used to as a measure of contextual fear conditioning.

Following the contextual testing, mice were returned to their home cages and all equipment was cleaned with 70% ethanol. Three hours after the contextual fear test, the mice were placed in the same test chambers, but with an altered floor and wall context. Animals were observed for 5 minutes of baseline activity followed by 5 audio tones identical to those presented in the training phase (5 kHz, 70 dB). Each 30 second tone was separated by 30 seconds of silence for a total of 10 minutes spent in the test chamber. The percentage of time spent freezing during the baseline phase and during the tone phase was used as a measure of the cued fear conditioning response.

Detection of Aβ and Immunohistochemistry.

Hippocampi were homogenized in modified RIPA buffer with protease inhibitor on ice. Protein concentrations were determined using the Bradford assay. Immunoblots were performed using 45 μg of total protein extract separated on 4-12% SDS-PAGE gels and then transferred electrophoretically to a 22 μm nitrocellulose membrane. Membranes were blocked with 5% milk in TBS-t, washed in TBS-t and incubated overnight at 4° C. in a primary 6E10 antibody (1:1000, Santa Cruz Biotechnology, Inc., Santa Cruz, Calif.) or actin (Sigma-Aldrich; St. Louis, Mo.). Membranes were then incubated in a secondary antibody solution for 30 minutes (1:5000, then in the presence of horseradish peroxidase-conjugated anti-mouse or anti-rabbit IgG) for 30 minutes. The optical density of immunoreactive bands was detected and quantified by chemiluminescence using the ECL system.

Immunohistochemical analyses were carried out on sections (~5 μm thick) of paraffin-embedded mouse brains. In brief, the sections were deparaffinized before being exposed to citrate buffer (0.01 M, pH 6.0) by heating in a microwave for 3 minutes and treated with 0.3% hydrogen peroxide in methyl alcohol for 20 minutes to block endogenous peroxidase activity. Aβ plaques were stained by incubating overnight at 4° C. with Aβ antibody #2454 or control isotype-matched antibody (Cell Signaling Technology, Danvers, Mass.), and detected with anti-rabbit biotinylated secondary antibody and avidin-biotin peroxidase complex (Vector Elite Kit; Vector Laboratories, Inc., Burlingame, Calif.), and diaminobenzidine (DAB) using a peroxidase substrate kit (Vector Laboratories). Before being mounted, the sections were counterstained with hematoxylin.

For quantification, digitized images of immunostained sections were obtained with a Qimaging Retiga 2000 SVGA FAST 1394 cooled digital camera system with 1600×1200 pixel array with 12-bit, 20 MHz digitization camera mounted on a NIKON 80i Research Upright Microscope using IP lab software (BD Biosciences-Bio-imaging).

Negative stain immunoelectron microscopy (IEM) was performed using 1 μl of samples placed on a carbon-coated collodion-filmed nickel grid and allowed to air dry. The samples were blocked using a goat blocking buffer and incubated with 6E10 antibody. After incubation with anti-mouse immunogold secondary antibody, samples were washed with 50 mMTris (pH 7.2) containing 125 mM NaCl, 0.1% (W/V) BSA, and Tween-20 (0.05%). The samples were stained by uranyl acetate (0.5% aqueous solution) and examined in the electron microscope (Hitachi H7600, Tokyo, Japan). The images were captured by a digital CCD camera and analyzed with AMT software (Danvers, Mass.). Immunogold secondary antibody, collodion, uranyl acetate, and blocking buffer were from Electron Microscope Sciences (Hatfield, Pa.).

Figure 4:
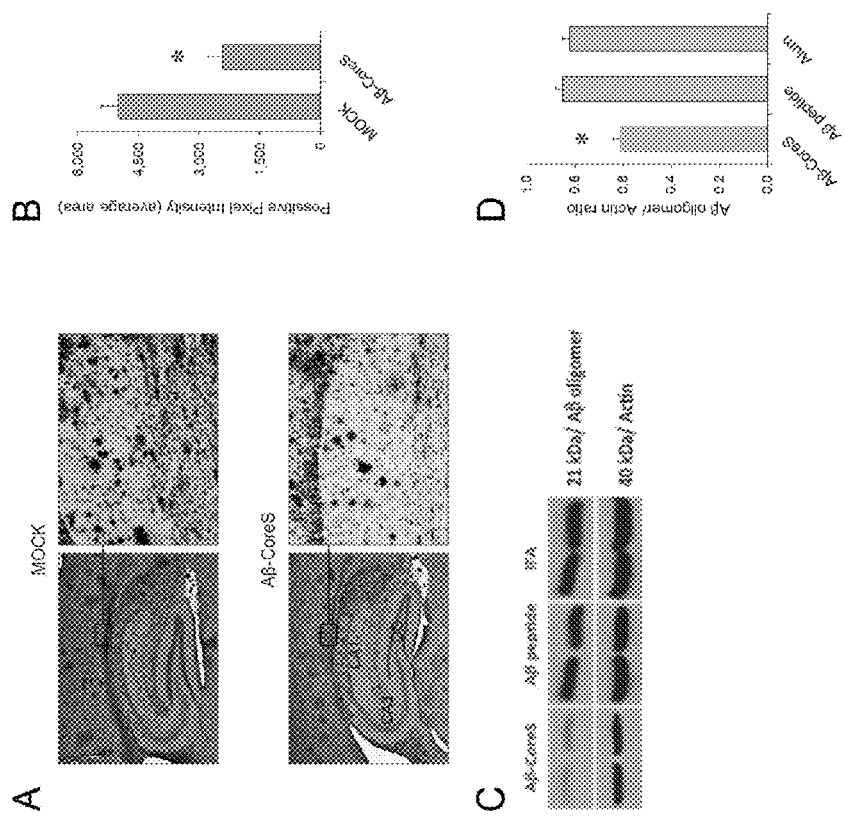
FIG. 4.

Results from the tests described above showed that Aβ-CoreS vaccine reduced Aβ plaques, improved cognition, and extended survival of 3xTgAD mice. Compared with the mock-treated group, immunizations with Aβ-CoreS started in 12 month-old 3xTgAD mice significantly reduced the accumulation of Aβ plaques in the hippocampus of 15 month-old mice, as revealed by immunohistochemical analysis (FIG. 4A, 4B) and western blot hybridization (FIG. 4C, 4D).

In contrast, immunizations with Aβ(1-42) peptide failed to reduce Aβ plaques in 3xTgAD mice, correlating with its inability to induce humoral responses (FIG. 2A). Importantly, compared with control treatment, 3xTgAD mice immunized with Aβ-CoreS exhibited enhanced hippocampus-dependent cognitive learning, as they exhibited enhanced freezing behavior in the contextual fear conditioning task (FIG. 5A).

Neuropsychiatric symptoms and anxiety impairments in particular are common in patients with mild cognitive impairments and are significant clinical predictors of earlier conversion to AD. The elevated plus maze is the gold-standard test to assess anxiety in mice. In this task, lower anxiety levels result in higher amounts of time spent in the open arms of the elevated plus maze, rather than in the relative safety of the closed arms. Compared with mock-immunized mice, Aβ-CoreS-immunized mice spent more time in the open arm of the elevated plus maze (FIG. 5B), suggesting that Aβ-CoreS also modified behaviors other than cognitive function in the 3xTgAD mice.

Figure 5:
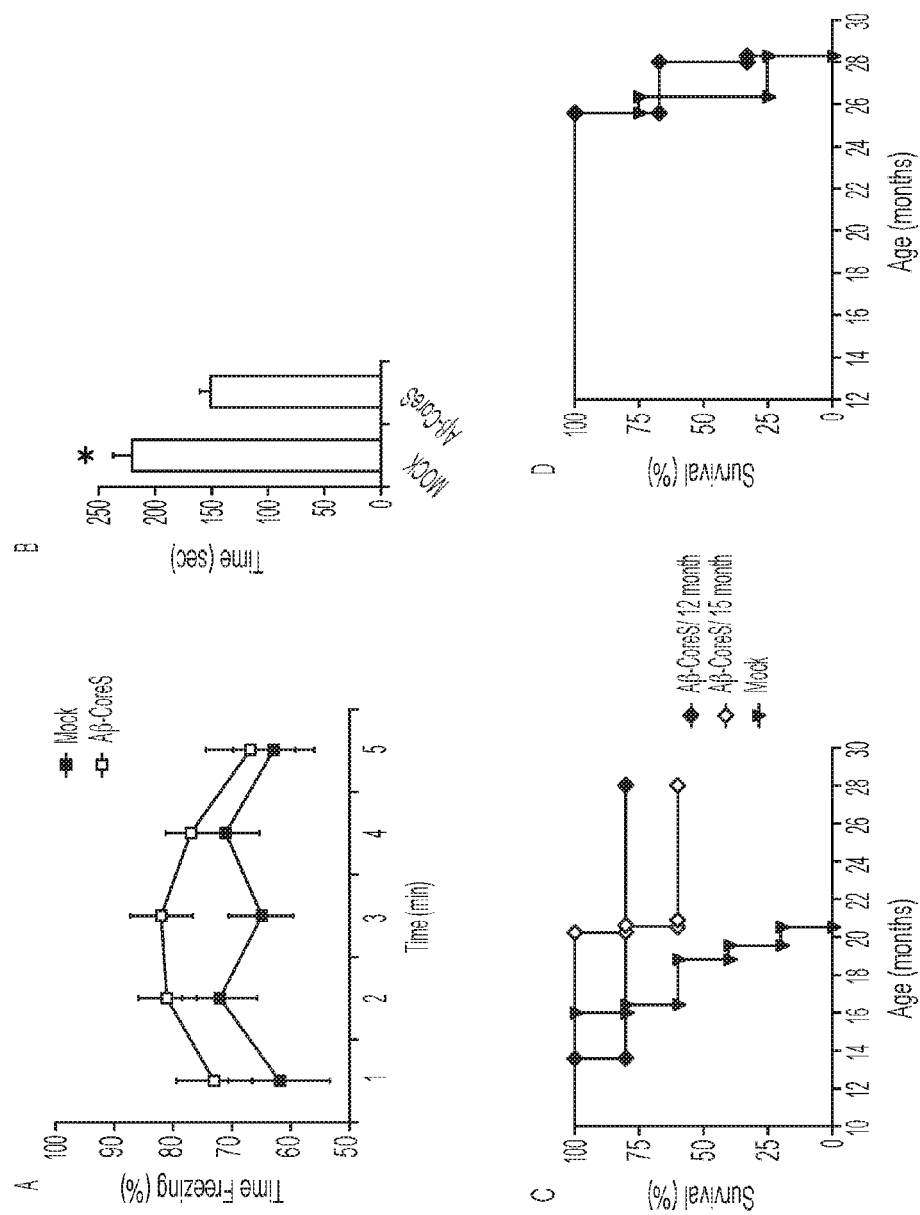
FIG. 5.
Figure 6:
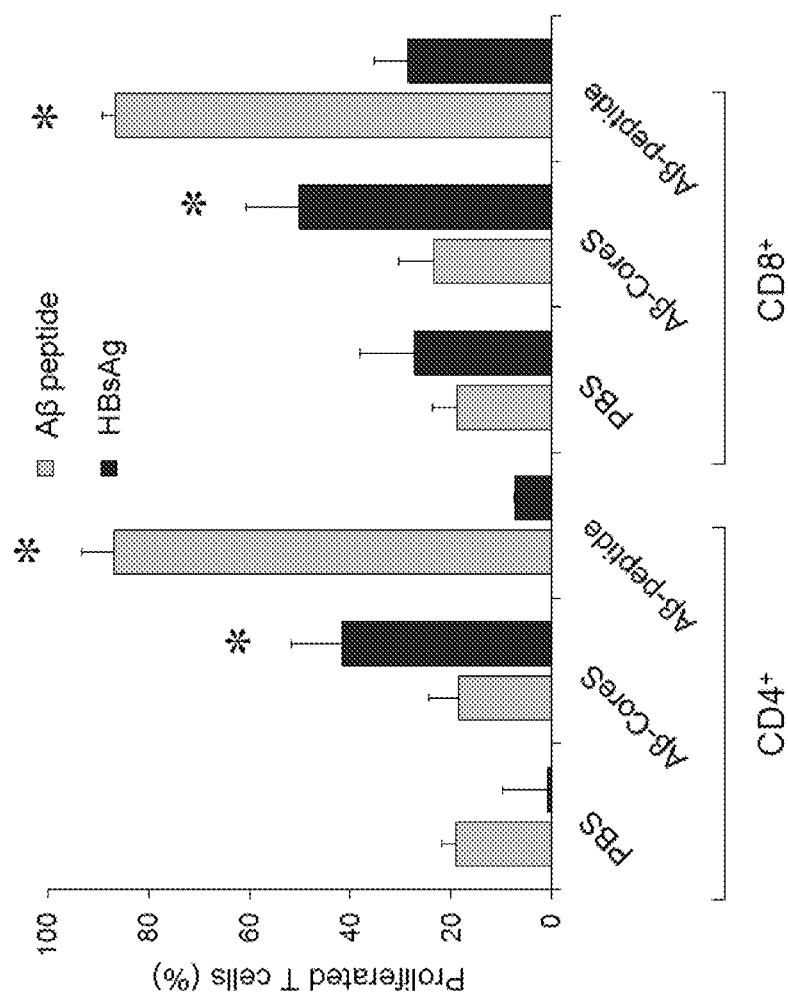
FIG. 6.

3xTgAD mice have a relatively short life span, with less than 25% of the mice surviving until 20 months of age after mock-treatment or DNA immunizations with S antigen (FIG. 5C). In contrast, more than 70% of the 3xTgAD mice immunized with Aβ-CoreS when they were 12 months old were alive by 28 months of age, when the experiment was terminated (FIG. 5C). Importantly, Aβ-CoreS immunizations initiated at 15 months of age also significantly prolonged survival (FIG. 5C). However, the survival benefit of the vaccine was lost in the few naturally surviving 3xTgAD mice that were immunized at 20 month of age (FIG. 5D), presumably due to the advanced stage of the disease.

CONCLUSIONS

Taken together, these Examples demonstrate that vaccination with Aβ(1-11) expressed on the surface of HBsAg particles elicited high levels of anti-Aβ antibody in both young and old mice. Importantly, in the AD model 3xTgAD mice, the vaccine reduced Aβ plaques, ameliorated cognitive impairments, and, surprisingly, significantly increased life span. Vaccines targeting Aβ(1-11) as disclosed herein therefore can efficiently combat AD-induced pathological alterations and provide survival benefit in patients with AD. The disclosed vaccines may also provide survival benefits including increased life span in the absence of AD or a diagnosis of AD.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

The invention claimed is:

1. An immunogenic composition comprising a DNA plasmid containing and expressing in vivo a polynucleotide, wherein said polynucleotide expressed by said plasmid comprises (i) a polynucleotide sequence encoding an antigenic polypeptide, (ii) a polynucleotide sequence encoding a T-helper epitope of hepatitis B virus capsid antigen, wherein the T-helper epitope of hepatitis B capsid antigen has the amino acid sequence of SEQ ID NO: 2; and (iii) a polynucleotide of S gene of hepatitis B virus, wherein said antigenic polypeptide comprises a fragment of amyloid-β protein.

2. The immunogenic composition of claim 1, wherein said antigenic polypeptide has the amino acid sequence of SEQ ID NO: 1.

3. The immunogenic composition of claim 1, wherein the DNA plasmid comprises a polynucleotide encoding the amino acid sequence of SEQ ID NO: 3, which includes polynucleotides (i), (ii) and (iii).

4. The immunogenic composition of claim 1, wherein said polynucleotide expressed by said plasmid is SEQ ID NO: 4.

5. The immunogenic composition of claim 1, wherein the DNA plasmid is in the circular plasmid form, wherein the plasmid additionally comprises an origin of replication, a promoter, and a transcription termination sequence.

6. An immunogenic composition comprising a DNA plasmid containing and expressing in vivo a polynucleotide, wherein said polynucleotide expressed by said plasmid comprises (i) a polynucleotide sequence encoding an antigenic polypeptide; (ii) a polynucleotide sequence encoding a T-helper epitope of hepatitis B virus capsid antigen, wherein the T-helper epitope of hepatitis B capsid antigen has the amino acid sequence of SEQ ID NO:2; (iii) a polynucleotide of S gene of hepatitis B virus; and (iv) a ligand, wherein said antigenic peptide comprises a fragment of amyloid-β protein, and wherein said composition comprises at least one adjuvant.

7. The immunogenic composition of claim 6, wherein said antigenic polypeptide has the amino acid sequence of SEQ ID NO: 1.

8. The immunogenic composition of claim 6, wherein said polynucleotide encoding an antigenic polypeptide is a polynucleotide encoding amino acids 1-11 of amyloid-β protein.

9. The immunogenic composition of claim 6, wherein said ligand specifically binds to the receptor CCR6 expressed on an immature dendritic cell.

10. The immunogenic composition of claim 6, wherein said ligand is a chemokine.

11. The immunogenic composition of claim 10, wherein said chemokine is MIP-3α.

12. The immunogenic composition of claim 6, wherein said ligand is a human β-defensin.

13. The immunogenic composition of claim 6, wherein said adjuvant comprises a cationic lipid and a neutral phospholipid in an aqueous vehicle.

14. An immunogenic composition comprising a DNA plasmid containing and expressing in vivo a polynucleotide, wherein said polynucleotide expressed by said plasmid comprises (i) a polynucleotide sequence encoding an antigenic polypeptide, (ii) a polynucleotide sequence encoding a T-helper epitope of hepatitis B virus capsid antigen; and (iii) a polynucleotide of S gene of hepatitis B virus, wherein said antigenic polypeptide comprises a fragment of amyloid-β protein, and wherein the DNA plasmid containing and expressing said polynucleotide encodes the amino acid sequence of SEQ ID NO:3, which includes polynucleotides (i), (ii) and (iii).

15. The immunogenic composition of claim 14, wherein said antigenic polypeptide has the amino acid sequence of SEQ ID NO: 1.

16. The immunogenic composition of claim 14, wherein the T-helper epitope of hepatitis B capsid antigen has the amino acid sequence of SEQ ID NO: 2.

17. An immunogenic composition comprising a DNA plasmid containing and expressing in vivo a polynucleotide, wherein said polynucleotide expressed by said plasmid comprises (i) a polynucleotide sequence encoding an antigenic polypeptide, (ii) a polynucleotide sequence encoding a T-helper epitope of hepatitis B virus capsid antigen; and (iii) a polynucleotide of S gene of hepatitis B virus, wherein said antigenic polypeptide comprises a fragment of amyloid-β protein, and wherein the polynucleotide expressed by said plasmid is SEQ ID NO:4.

18. The immunogenic composition of claim 17, wherein said antigenic polypeptide has the amino acid sequence of SEQ ID NO: 1.

19. The immunogenic composition of claim 17, wherein the DNA plasmid is in the circular plasmid form, wherein the plasmid additionally comprises an origin of replication, a promoter, and a transcription termination sequence.

20. The immunogenic composition of claim 17, wherein the T-helper epitope of hepatitis B capsid antigen has the amino acid sequence of SEQ ID NO: 2.

* * * * *

```
                          SEQUENCE LISTING

<160> NUMBER OF SEQ ID NOS: 6

<210> SEQ ID NO 1
<211> LENGTH: 11
<212> TYPE: PRT
<213> ORGANISM: Homo sapiens

<400> SEQUENCE: 1

Asp Ala Glu Phe Arg His Asp Ser Gly Tyr Glu
1               5                   10

<210> SEQ ID NO 2
<211> LENGTH: 16
<212> TYPE: PRT
<213> ORGANISM: Hepatitis B virus

<400> SEQUENCE: 2

Val Asp Thr Leu Ala Thr Trp Val Gly Gly Asn Leu Glu Asp Leu Asp
1               5                   10                  15

<210> SEQ ID NO 3
<211> LENGTH: 270
<212> TYPE: PRT
<213> ORGANISM: Artificial Sequence
<220> FEATURE:
<223> OTHER INFORMATION: Fusion protein

<400> SEQUENCE: 3

Met Val Asp Thr Leu Ala Thr Trp Val Gly Gly Asn Leu Glu Asp Leu
1               5                   10                  15

Asp Gly Gly Gly Gly Ser Asp Ala Glu Phe Arg His Asp Ser Gly Tyr
                20                  25                  30

Glu Ala Ser Ser Arg Ile Gly Asp Pro Ala Leu Asn Met Glu Asn Ile
            35                  40                  45

Thr Ser Gly Phe Leu Gly Pro Leu Leu Val Leu Gln Ala Gly Phe Phe
        50                  55                  60

Leu Leu Thr Arg Ile Leu Thr Ile Pro Gln Ser Leu Asp Ser Trp Trp
65                  70                  75                  80

Thr Ser Leu Asn Phe Leu Gly Gly Thr Thr Val Cys Leu Gly Gln Asn
                85                  90                  95

Ser Gln Ser Pro Thr Ser Asn His Ser Pro Thr Ser Cys Pro Pro Thr
            100                 105                 110

Cys Pro Gly Tyr Arg Trp Met Cys Leu Arg Arg Phe Ile Ile Phe Leu
            115                 120                 125
```

```
Phe Ile Leu Leu Leu Cys Leu Ile Phe Leu Leu Val Leu Leu Asp Tyr
    130                 135                 140

Gln Gly Met Leu Pro Val Cys Pro Leu Ile Pro Gly Ser Ser Thr Thr
145                 150                 155                 160

Ser Thr Gly Pro Cys Arg Thr Cys Thr Thr Pro Ala Gln Gly Thr Ser
                165                 170                 175

Met Tyr Pro Ser Cys Cys Cys Thr Lys Pro Ser Asp Gly Asn Cys Thr
            180                 185                 190

Cys Ile Pro Ile Pro Ser Ser Trp Ala Phe Gly Lys Phe Leu Trp Glu
        195                 200                 205

Trp Ala Ser Ala Arg Phe Ser Trp Leu Ser Leu Val Pro Phe Val
210                 215                 220

Gln Trp Phe Val Gly Leu Ser Pro Thr Val Trp Leu Ser Val Ile Trp
225                 230                 235                 240

Met Met Trp Tyr Trp Gly Pro Ser Leu Tyr Ser Ile Leu Ser Pro Phe
                245                 250                 255

Leu Pro Leu Leu Pro Ile Phe Phe Cys Leu Trp Val Tyr Ile
            260                 265                 270
```

<210> SEQ ID NO 4
<211> LENGTH: 813
<212> TYPE: DNA
<213> ORGANISM: Artificial Sequence
<220> FEATURE:
<223> OTHER INFORMATION: Fusion polynucleotide

<400> SEQUENCE: 4

```
atggtcgaca ctctagctac ctgggtgggt ggtaatttgg aagatctcga cggtggcggt      60
ggtagcgatg cagaattccg ccatgactca ggatatgaag cttcgtcgag gattggggac     120
cctgcgctga acatggagaa catcacatca ggattcctag acccctgct cgtgttacag      180
gcggggtttt tcttgttgac aagaatcctc acaataccgc agagtctaga ctcgtggtgg     240
acttctctca attttctagg ggaactacc gtgtgtcttg gccaaaattc gcagtcccca      300
acctccaatc actcaccaac ctcctgtcct ccaacttgtc ctggttatcg ctggatgtgt     360
ctgcggcgtt ttatcatctt cctcttcatc ctgctgctat gcctcatctt cttgttggtt     420
cttctggact atcaaggtat gttgcccgtt tgtcctctaa ttccaggatc ttcaactacc     480
agcacgggac catgcagaac ctgcacgact cctgctcaag gaacctctat gtatccctcc     540
tgttgctgta ccaaaccttc ggacggaaat tgcacctgta ttcccatccc atcatcctgg     600
gctttcggaa aattcctatg ggagtgggcc tcagcccgtt ctcctggct cagtttacta     660
gtgccatttg ttcagtggtt cgtagggctt ccccccactg tttggctttc agttatatgg     720
atgatgtggt attgggggcc aagtctgtac agcatcttga gtcccttttt accgctgtta     780
ccaatttctc tctgtctttg gtatacatt taa                                   813
```

<210> SEQ ID NO 5
<211> LENGTH: 9
<212> TYPE: PRT
<213> ORGANISM: Mus musculus

<400> SEQUENCE: 5

```
Glu Gly Ser Arg Asn Gln Asp Trp Leu
1               5
```

<210> SEQ ID NO 6
<211> LENGTH: 15

```
<212> TYPE: PRT
<213> ORGANISM: Artificial Sequence
<220> FEATURE:
<223> OTHER INFORMATION: MOPC-315 Ig (91-101)

<400> SEQUENCE: 6

Ala Leu Trp Phe Arg Asn His Phe Val Phe Gly Gly Gly Thr Lys
1               5                   10                  15
```